United States Patent [19]
Kindwall et al.

[11] Patent Number: 6,084,666
[45] Date of Patent: Jul. 4, 2000

[54] APPARATUS FOR MULTIPLE POSITIONING OF A PLANAR SAMPLE AT A REPEATABLE DISTANCE AND ANGLE FROM A TESTING DEVICE

[75] Inventors: Alexander P. Kindwall, San Francisco; Dale Buermann, Los Altos, both of Calif.

[73] Assignee: N+K Technology Inc., Santa Clara, Calif.

[21] Appl. No.: 09/233,692

[22] Filed: Jan. 19, 1999

[51] Int. Cl.⁷ .................................................. G01N 21/01
[52] U.S. Cl. .............................. 356/244; 74/18.2; 269/21; 248/181.1
[58] Field of Search ........................... 356/244, 36, 426; 74/18.2; 269/21; 248/181.1

[56] References Cited

U.S. PATENT DOCUMENTS

| | | | |
|---|---|---|---|
| 4,226,569 | 10/1980 | Gerard et al. | 414/737 |
| 4,781,520 | 11/1988 | Balter | 414/751 |
| 5,353,112 | 10/1994 | Smith | 356/244 |
| 5,579,113 | 11/1996 | Papst et al. | 356/244 |

*Primary Examiner*—Frank G. Font
*Assistant Examiner*—Roy M. Punnoose
*Attorney, Agent, or Firm*—Lumen Intellectual Property Services

[57] ABSTRACT

An apparatus for rotationally positioning a disk on a stationary stage at a constant and repeatable distance and angle for a device to perform an operation on several positions of the disk surface is disclosed. The disk apparatus has a manipulating member that operates from a central portion of the stationary stage. The member raises the disk, rotates the disk to a new position and sets the disk back down on a planar portion of the same stationary stage. The apparatus uses vacuum to secure the disk to the stage and to the member during manipulation. The member is raised by a spring and lowered by vacuum. The apparatus is easily incorporated into an optical system for performing reflectance and transmitance on both side of the disk simultaneously allowing for the analyses of the disk layers for composition and consistency.

40 Claims, 3 Drawing Sheets

APPARATUS FOR MULTIPLE POSITIONING OF A PLANAR SAMPLE AT A REPEATABLE DISTANCE AND ANGLE FROM A TESTING DEVICE

FIELD OF THE INVENTION

The present invention relates generally to an apparatus for manipulating planar samples on a stationary stage. More specifically, the present invention relates to an apparatus for manipulating the rotational position of a disk sample on a stationary stage for spectral analysis.

BACKGROUND OF THE INVENTION

U.S. Pat. No. 4,781,520 by Balter discloses a polar-coordinate manipulator for positioning a disk sample within a vacuum chamber while it is subjected to ion implantation or measurement procedures. Bellows extend from the polar manipulator to the vacuum chamber into which a sample holder extends. The sample holder remains in contact with the sample throughout its rotation and vertical translations within the vacuum chamber. This apparatus is not well suited manipulating a disk for spectral analysis.

Spectral analysis of disks depends strongly on the angle of incidence that the radiation strikes the disk. Such is the case with ellipsometric evaluation, in which the polarization of electromagnetic radiation is altered by the sample depending on the incident angle of the radiation. If the angle of the sample is changed during the sample measurements significant error is introduced into the method. However, if the angle of the sample relative to the optical measuring device is accurately known and controlled, information about number of disk layers and compositions of those layers can be derived from the spectral data.

For industrial applications the compositions of layers and the number of layers is often known and what is of interest to a manufacture of disk products is the consistency of the films that have been deposited on a disk substrate. Therefore, it is necessary to analyze several location on a disk. This can be accomplished by securing a disk to a rotating platform and rotating the disk and platform relative to a stationary measuring device. Rotating platforms described above are generally suspended by a low friction bearing. Unfortunately, even very precise bearing systems introduce enough angular variation in the sample to cause significant errors in spectral measurements. The angular variation of the planar surface of a disk in apparatus of this type are due to several circumstances; 1) The interacting components of the rotating platform may have been imperfectly machined, potentially causing tilting of the sample. 2) A rotating member may be non-perpendicular to the plane in which the sample is held, once again causing tilting. 3) Friction between rotating and static members of the rotating platform may cause uneven thermal expansion of components, again tilting the sample. Additionally, high precision rotating bearing systems used for rotating stages are very large, are very costly, and they physically prevent an operations or measurements from being performed on the bottom portion of the disk sample supported by the rotating platform.

U.S. Pat. No. 4,226,569 by Gerard et al. discloses a sample loader and leveling apparatus. The loading device secures the disk accurately on the stage, but leveling and rotation of the sample is once again accomplished by rotating sample stage similar to that described above and, therefore, suffers from the same disadvantages when integrated into a disk handling system that requires very repeatable and accurate angular positioning of a planar disk sample.

What is needed is an apparatus that can rotationally manipulate a planar sample on a platform, whereby the angle of the planar surface of the sample is consistently maintained from one position to the next. A possible solution is to rotate the device performing the operation or measurement on the sample relative to a static sample secured on a static platform. This is often cumbersome or impossible, depending on the equipment performing the operation or measurement. Further, moving the equipment will generally introduce far greater inaccuracies in the method of interest than does moving the sample. What is further needed is an apparatus for rotating a disk sample that is small and will allow operations or measurements on both sides of a planar sample, such as a disk, either independently or concurrently.

OBJECTS AND ADVANTAGES OF THE INVENTION

It is, therefore, an object of the present invention to provide an apparatus for rotationally adjusting a sample with a planar surface on a stationary stage. The apparatus rotates and positions the sample on a flat surface of the stationary stage for a stationary device, such as a spectrophotometer, to perform an operation on a plurality of positions of the sample. Because the stage is stationary, the planar surface of sample is positioned at a repeatable distance and angle from the stationary device.

It is also an object of the invention to provide an apparatus the rotationally positioning a planar sample on a stationary stage that is sufficiently small, whereby the bottom planar surface of the sample is accessible for performing operations and measurements. This has the advantage of allowing for analyses of both sides of a disk samples and eliminates the need for flipping a disk.

It is also an object of this invention to provide an apparatus for rotationally positioning a disk sample that is easily incorporated into optical system that can perform several measurement of a disk sample at a plurality of positions for measuring and analyzing disk layer thicknesses, compositions an uniformity.

SUMMARY OF THE INVENTION

The invention is an apparatus for quickly and accurately positioning a sample with a planar surface at a repeatable distance and angle from a stationary device that performs the operation. Most importantly, the device is used for manipulation of a disk wafer relative to a spectrophotometer for performing transmitance and reflectance measurements on the disk. The apparatus comprises a stationary stage that is preferably a metal stage with a smooth machined flat surface but can also be any resilient material that can be machined such as Teflon® or plastic. Stationary stage herein, means a stage that does not move rotationally and does not rotationally repositioning the sample. The stationary stage is, however, not limited to a fixed position and can be translated itself by another means in any direction. The apparatus is capable of raising, rotating a disk and then positioning the disk on the flat surface of the stationary stage. Because the stationary stage is not moving rotational, each position that the disk is rotated to is repositioned on the stage at a reproducible distance and angle and thus provides consistent positioning of the sample for consecutive measurements or operations.

The stationary stage preferably has a central bore, or hollowed out section for a lifting aperture to move within. The bore is preferable centrally positioned and cylindrical with the length of the cylindrical bore being perpendicular to the flat surface of the stationary stage. In one embodiment of the invention, a lifting aperture is cylindrical piston, preferably polished metal with a flat top portion and an outer diameter essentially equal to diameter of the bore. The piston is positioned within the bore and is used for supporting the disk during lifting, rotating and lowering of the disk. The lifting aperture can also be a lifting stage that is configured as a plurality of fingers. What is important is that the lifting aperture is capable of supporting and securing the sample during lifting and rotation of the sample.

The disk sample is secured to the stationary stage during the spectral measurements by a vacuum source that is drawn through an orifice in the flat surface of the stationary stage and the sample is secured to the piston during manipulation of the sample position by a vacuum source drawn through an orifice in the top flat portion of the piston. A controller device is used to release the vacuum from the stationery stage when the disk sample is being manipulated. Alternatively, the sample is secured to the stationary stage and the piston by a single vacuum source that is drawn through an orifice in the top flat portion of the piston, whereby the piston is lowered below the flat surface of the stationary stage to secure the sample. In this embodiment the wall of the bore and the piston form a substantially air tight seal.

The piston is connected to a shaft that extends through the center of the bore to at least one support bushing positioned below the bore to hold the shaft central during rotational operations. Both the shaft and piston are capable of moving in an upward and downward motion. The piston is preferable moved using the shaft but can be moved by a pneumonic device or a solenoid attached to the wall of the bore and positioned under the bottom of the piston. In the preferred embodiment a bottom portion of the shaft is connected to a spring. The spring exerts a continuous upward forces on the shaft, whereby the piston is in a raised position in the absence of a greater downward force being exerted on the shaft or the connected piston to overcome the continuous upward force of the spring. In this embodiment a cylindrical piston and a cylinder bore form an essential air tight seal and the bottom of the piston and a portion of the bore form a vacuum camber. A vacuum source is drawn through an orifice in the wall of the bore below the piston, whereby a vacuum is capable of causing a downward force on the piston to overcome the upward force of the spring and thus lowering the piston. The lowest position that the piston can be lowered to, within the bore, is controlled by a piston stopper. The piston stopper protrudes from the inside wall of the bore such that the piston is prevented from being lowered farther than a position where the bottom of the piston and the piston stopper come in contact.

The shaft can be turned by any means such as belts and a worm gears. The shaft is preferably turned by a first gear attached to the shaft and a second gear attached to a stationary motor, whereby the first gear and second gear engage when the shaft is in the raised position. The shaft is turned by the stationary motor turning the second gear and translating the rotational motion to the first gear attached to the shaft. The motor is preferably an electrical stepper motor that rotates the shaft in known incremental degrees of rotation. Preferably, the motor is further attached microprocessor that registers the positions of the disk sample during spectral measurement and correlates the position data with the spectral data, thus providing information about layer consistencies within the sample.

An alternative embodiment of the invention comprises a circular disk platform connected to a centrally attached shaft for supporting the disk sample. The shaft passing centrally through a chamber that houses at least one piston for lowering the sample platform. In this embodiment a spring and a supporting bushing is attached to the shaft as described above and the gears for rotating the shaft are also as described above.

The circular disk platform moves in an upward and downward direction within a recession well. The disk platform is connected to a shaft capable of raising the disk platform above the flat surface of the stationary stage, rotating the disk platform, and lowering the disk platform to a position below flat surface of the stationary stage. A vacuum source is used to secure a disk sample to both the disk platform and the flat surface of the stationary stage. The vacuum is drawn through at least one orifice on a flat top surface of the disk platform. Preferably, the vacuum is drawn through the shaft that is hollow and is connected to the orifice in the flat top potion of the circular disk platform. The circular disk platform further comprises a raised circular portion centrally located on the disk platform, whereby a disk with a central circular cut out of the same size as the raised portion of the disk platform will be held centrally on the disk platform.

In the above embodiment a preferred method for lowering the disk platform is cylindrical isolated chamber positioned between the disk platform and a spring attached to the bottom of the shaft. The shaft passes through the center of the chamber and two cylindrical pistons. A first cylindrical piston has a diameter substantially equal to diameter of the cylindrical chamber, whereby the first piston and the chamber wall form a substantially air tight seal. The first piston is not rigidly secured to the shaft and can slide in an upward and downward motion on the shaft, but is prevented from sliding downward on the shaft past a point where a stop ring is attached. Further the piston is can not go downward in the chamber past a position of a first piston stop that is a protrusion on the inside wall of the chamber. Therefore, a downward force of sufficient strength to overcome the spring force applied to the first piston will lower the disk platform to a first lowered position. A second piston is position on the shaft below the first piston. The second piston forms a substantially air tight seal between the chamber wall and the second piston and is capable of moving on the shaft but will not move upward on the shaft past the position of a second piston stop that is a protrusion on the inside wall of the chamber. The bottom of the first piston and top of the second piston form a first vacuum chamber. A vacuum source is connected to an orifice in the wall of the first vacuum chamber and is capable of lowering the first piston and the sample stage to the first lowered level. A second stop ring attached to the shaft below the second piston prevents the second piston from sliding down on the shaft past the position on the shaft where the stop ring is attached. The bottom of the second piston and the bottom of the chamber form a second vacuum chamber. A vacuum source is connected to an orifice in the wall of the second vacuum chamber and is capable of lowering the second piston and the sample stage to a second lowered level. This embodiment provides for an apparatus that is capable of lowering the disk platform to two position. The first lowered position secures a disk sample with a circular central cut out to the flat surface of the stationary stage. The second position places the entire disk platform below the flat surfaces of the stationary stage so that a planar sample without a circular cut out can be held securely to the flat surface of the stationary stage.

The most preferred embodiment of the invention is an apparatus that rotationally positions a disk sample by the inner diameter region of the disk. The stationary stage is sufficiently small that a optical device can measure the entire useful portion of the disk from the underside of the disk without physical interference from device.

DETAILED DESCRIPTION

Figure 1:
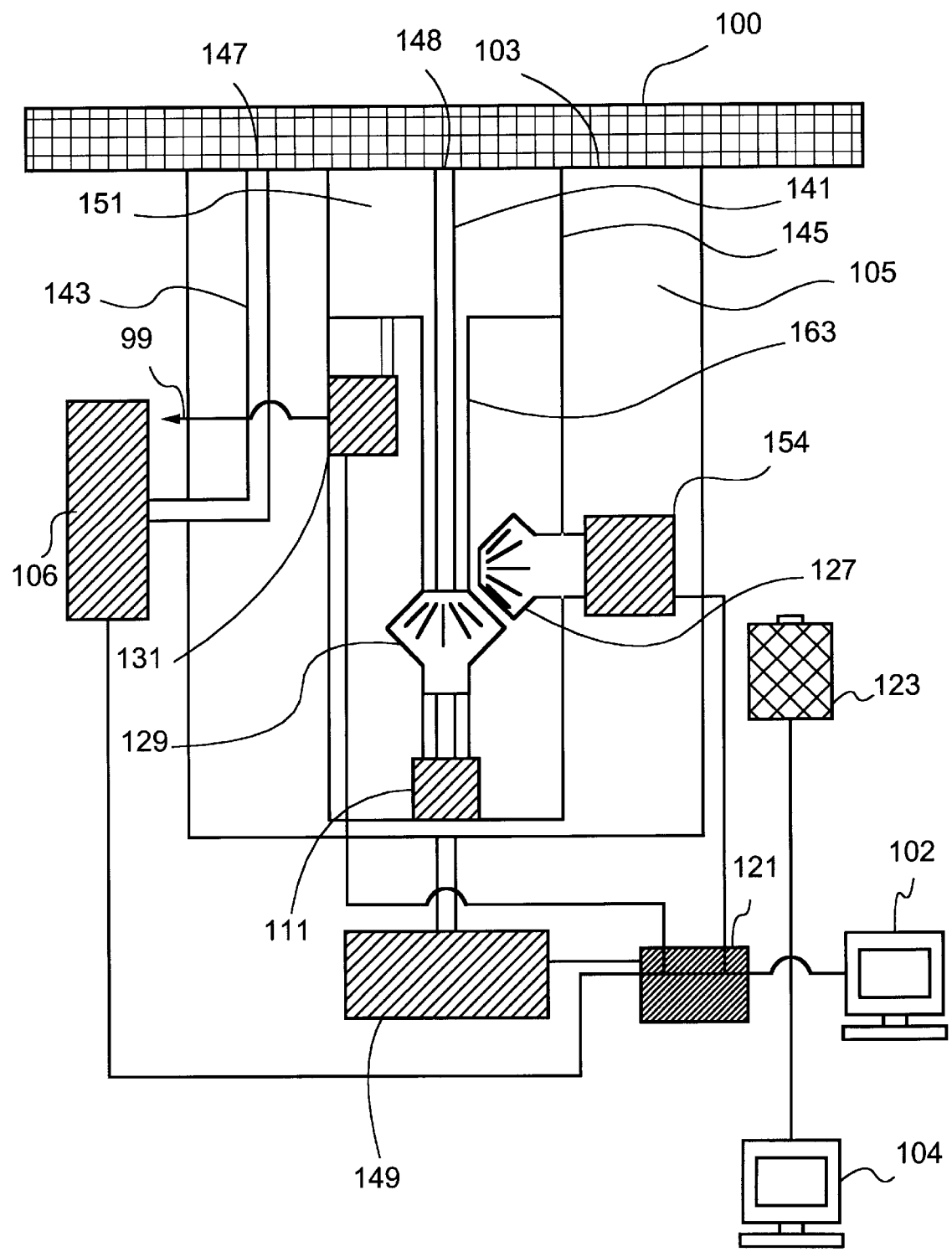
FIG. 1 shows a cross-sectional view an apparatus for positioning a planar sample a repeatable distance and angle from a testing device on a stationary stage.

In reference to FIG. 1, a sample 100 rests on a flat surface 103 of the stationary stage 105. A substantially central bore 145 within the stationary stage 105 houses a lifting aperture that is preferably a cylindrical piston 151 with a flat top portion 103 for supporting the sample 100 during raising and rotation. A shaft 163 is connected to the piston 151 and supported in the bottom of the bore 145 with a bushing 111 to hold the shaft central in the bore. A device 131 controls the vertical positioning of the piston 151. The device 131 is preferably a pneumatic device but can also be a mechanical spring or a solenoid. For rotationally manipulating the sample 100, the piston 151 is positioned above the flat surface 103 of the stationary stage 105, the sample is rotated with the piston in the raised position and the piston 151 is lowered to place the sample 100 in a new rotational position on the same stationary stage 105.

The piston 151 is rotated by any means such as a pulley or worm gear but is preferably rotated by the connected shaft 163 with a first gear 129 attached to the shaft 163 and a second gear 127 that is attached to a stationary motor 154. The motor 154 is preferably a stepper motor that registers its incremental positioning of the piston 151. When the piston 151 is in the raised position (not shown) the first gear 129 and the second gear 127 engage and the motor will be able to rotate the gears, the attached shaft 163 and the piston 151.

The sample 100 is secured to the flat surface 103 of the stationary stage 105 and to the piston 151, preferably through a vacuum source. A vacuum source 106 draws a vacuum through a duct 143 that is connected to an orifice 147 in the flat surface 103 of the stationary stage 105 and secures the sample 100 to the stage 103. During manipulation of the sample 100, a second vacuum source 149 draws a vacuum through a duct 141 in the shaft 163 that is connected to an orifice 148 in the top portion of the piston 151.

The vacuum sources 106/149 and the pneumatic device 131 are connected to a central controller 121 and a computing micro-processor 102. The vacuum 106 is on only when the sample 100 is resting on the stationary stage 105, which means the top portion of the piston 151 is below the flat surface 103 of the stationary stage 105. The piston vacuum 149 is on when the sample 100 is supported by the piston 151 during raising and rotation of the sample 100. Preferably, only one of the two vacuum sources are running at a given moment, and are switched when the piston 151 passes the flat surface 103 of the stationary stage 105.

The apparatus can be used for any device 123 to perform an operation on a plurality of positions, but the preferred device 123 is a spectrophotometer for measuring reflectance and transmitance. Also shown is a computing microprocessor 104 capable of analyzing the composition and consistency the sample 100 from reflectance and transmitance spectra.

Figure 2:
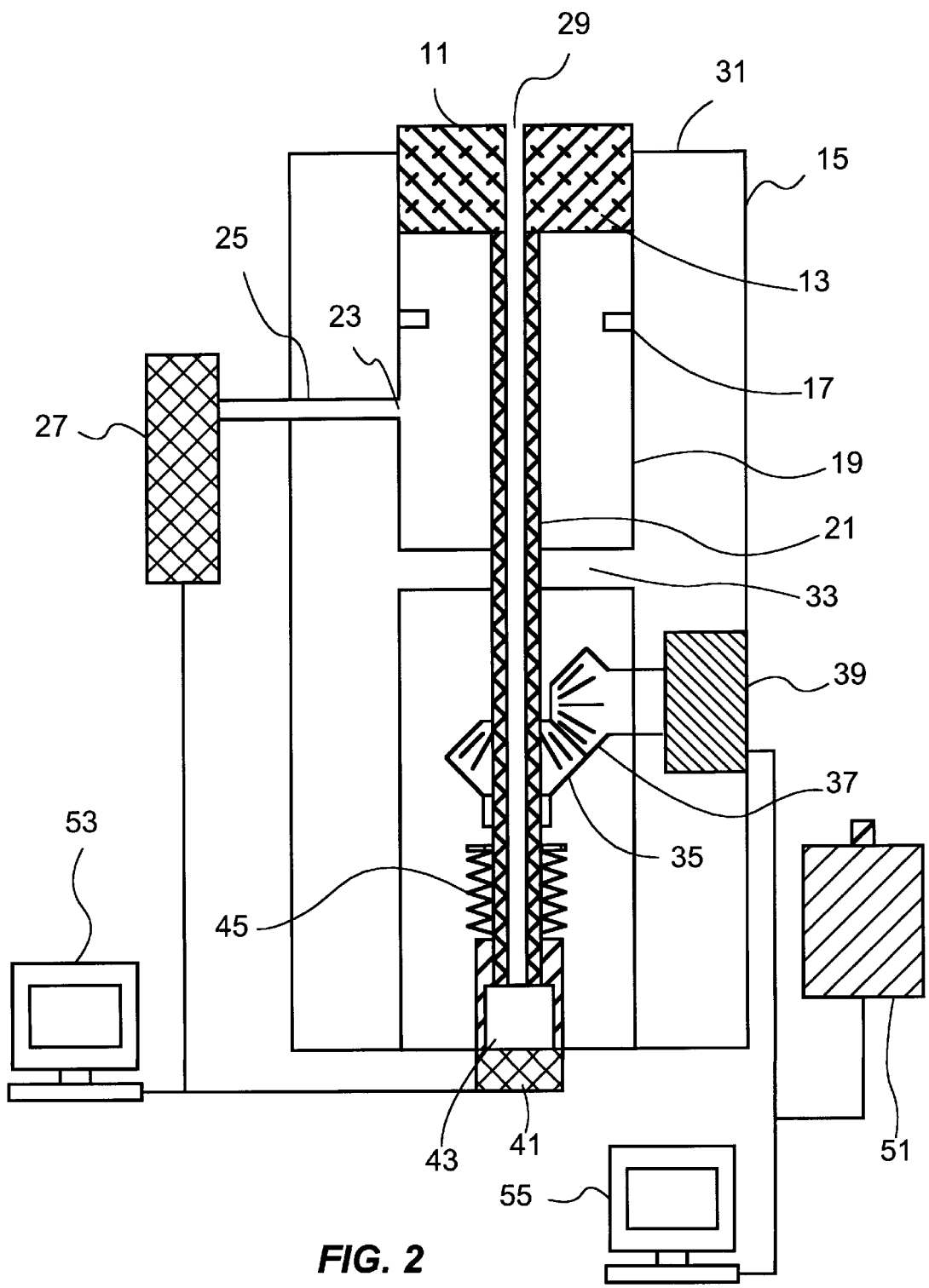
FIG. 2 shows a cross-sectional view an apparatus for positioning a planar sample a repeatable distance and angle from a testing device with a spring and a vacuum chamber for raising and lowering a planar sample.

Referring to FIG. 2, an alternative embodiment of the invention is a stationary stage 15 a flat surface 31 for supporting a disk sample. The flat surface 31 is preferably a metal surface that is machined smooth. A substantially central bore 19 within the stationary stage 15 houses a cylindrical piston 13 with a flat top portion 11 for supporting the sample during raising and rotation. A shaft 21 is connected to the piston 13 and supported in the bottom of the bore 19 with a bushing 43. In this embodiment the shaft is capable of raising, rotating and lowering the piston 13. By raising the shaft 21, a first gear 35 attached to the shaft 21 engages a second gear 37 that is attached to a stationary motor 39. Once in this arrangement, the shaft 21 and piston 13 can be rotated by the stationary motor 39. Following rotation, the top portion 11 of the piston 13 recesses below the flat surface 31 of the stationary stage 15, and the sample is released onto the stationary stage 15.

The shaft 21 is raised by the upward force of a spring 45 attached to its lower portion. The spring 45 provides continuous upward force, maintaining the piston 13 in a raised position unless a greater downward force is exerted on the shaft 21 to overcome this force. A partition 33 in the substantially central cylindrical bore 19 creates two sections; the lower of which encloses the rotator gears 35,37 and spring 45 and the upper chamber serves to house the piston. A section of the upper chamber, below the piston 13 serves a vacuum chamber, whereby drawing a vacuum on the vacuum chamber lowers the piston 13.

A piston stop 17 that is a protrusion of the bore positioned within the upper section of the bore 19 to prevents the piston 13 from moving downward in the upper section of the bore 19 beyond the point at which the piston stop 17 is attached to the wall of the upper section 19. A vacuum source 27 is connected to the upper section of the cylindrical bore 19 by duct 25 that is connected to an orifice 23 between the piston stopper 17 and the partition 33.

The sample is secured to the stationary stage 15 and to the piston 13, preferably through a vacuum. A vacuum source 41 draws a vacuum through an orifice 29 in the shaft 21 which extends through the top portion 11 of the piston 13 and secures the sample when in contact with the piston 13. Further the same vacuum source secures the sample to the flat surface 31 of the stationary stage 15 when the flat top portion 11 of the piston 13 has receded below the flat surface 31 of the stationary stage 15. In a preferred embodiment both vacuum sources 27,41 and the stepper motor 39 are connected to a computing micro-processor 53 that controls vacuums and positioning of the sample.

Additionally, the apparatus is preferably integrated with an optical device 51, such as a spectrophotometer for measuring reflectance and transmitance. The spectrophotometer 51 is connected to a micro-processor 55 that is capable of computing disk layer thicknesses and disk layer compositions from reflectance and transmitance measurements. The micro-processor 55 is further connected to the stepper motor 39 to register the position of the sample and further provide information about the consistency of disk layers within a disk sample.

Figure 3:
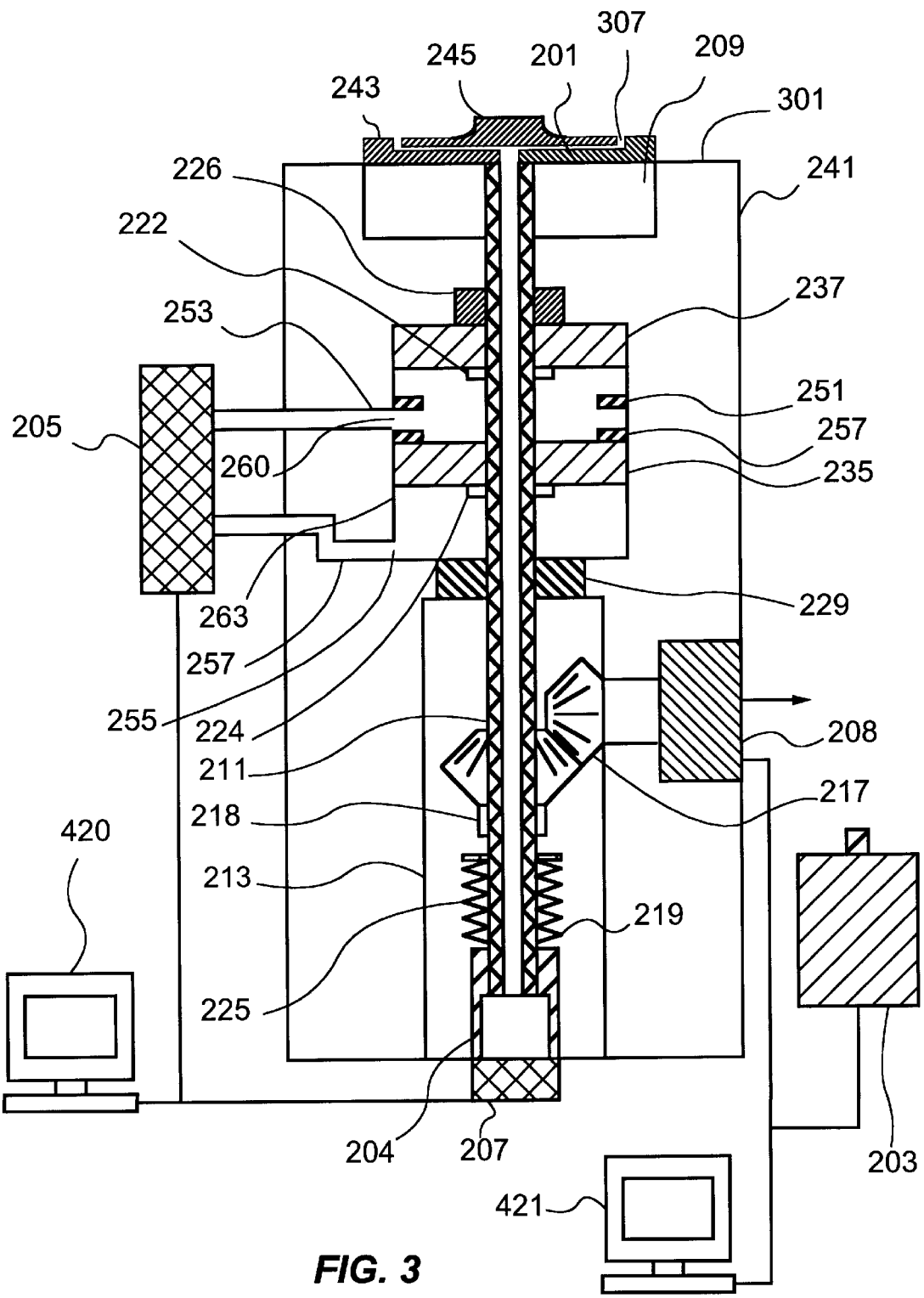
FIG. 3 shows a cross section an apparatus for positioning a disk a repeatable distance and angle a spectraphotometer with a spring for raising the sample stage a two pistons for lowering the sample stage to two different positions.

Referring to FIG. 3, the apparatus has a flat surface 301 to support a sample (not shown). Preferably the flat surface 301 is a machined smooth metal surface. A substantially central cylindrical recession well 209 is position in the top of the stationary stage 241 for housing a circular disk platform 201. The circular disk platform 201 (shown in a raised position) has substantially the same diameter as the recession well 209 and with a flat top portion 243 for supporting the disk during raising and rotation. A raised circular portion 245 is positioned centrally on the platform 201 for centrally supporting a disk on the platform 201 when the disk has a central circular cut out. A shaft 211 is connected to the platform 201 and extends centrally through the bottom of the recession well 209, through the center of a cylindrical vacuum chamber 263 and to the bottom of the stationary stage 241 where the shaft 211 is supported by a bushing 204. Preferably additional bushings 229 and 226 are encased in the stationary stage 241 to provide stabilization for the shaft 211. The cylindrical chamber 263 has a predetermined diameter and length with the length being parallel to the shaft 211. A second chamber 213 is positioned below the vacuum chamber 263 and houses a gear assembly for rotating the shaft 211 and the disk platform 201.

The shaft 211 is raised by the upward force of a spring 225 attached to the shaft 211. The spring 225 provides continuous upward pressure maintaining the platform 201 in the raised position unless a greater downward force is exerted on the shaft 211 to overcome this force. When the shaft 211 is in the raised position, a first gear 218, attached to the shaft 211, engages a second gear 217 that is attached to a stationary motor 208. In the raised position, the shaft 211 and disk platform 201 can be rotated by the stationary motor 208, preferably a stepper motor.

The disk platform 201 is lowered by the vacuum chamber 263. A first piston 237 is housed in the vacuum chamber 263. The first piston 237 has a diameter that is substantially equal to the diameter of the vacuum chamber 263 and forms an essentially air tight seal between the wall of the cylindrical vacuum chamber 263 and the first piston 237. The first piston 237 is not secured to the shaft 211 and is capable of moving upward and downward on the shaft 211, but is prevented form moving downward on the shaft 211 past the position on the shaft 211 where a first piston stop ring 226 is attached. Further, the first piston is prevented from moving downward within the chamber past the position where a first piston stop 251 is attached to the wall of the chamber 263. Below the first piston stop is a second piston stop 257 that prevents a second piston 235 from moving upward in the chamber 263 past the position in the chamber where the second piston stop 257 is attached. The second piston 235 has substantially the same diameter as the chamber 263 and forms and essentially air tight seal between the chamber wall and the second piston 235. The second piston 235 is not secured to the shaft 211, but is prevented from moving downward on the shaft 211 past the position where a second stop ring 224 is attached to the shaft 211.

When a vacuum is drawn on the top section of the vacuum chamber between the bottom of the first piston and the top of the second piston, the shaft 211 and the disk platform 201 is lowered to a first lowered position. Further when a vacuum is applied to the lower section of the chamber defined by the bottom of the chamber and the bottom of the second piston the shaft 211 and the disk platform 201 is lowered to a second lowered position.

The disk is secured to the flat surface 301 of the stationary stage 241 and to the platform 201, through a vacuum. A vacuum source 207 draws a vacuum through a center bore 219 of the shaft 211 that is connected to at least one orifice 307 around the perimeter of the top flat portion 243 of the disk platform 201. Further, the same vacuum source 207 secures the disk to the flat portion 301 of the stationary stage 241 when the flat top portion 243 of the disk platform 201 is lowered bellow the flat portion 301 of the stationary stage 241.

The vacuum source 205 draws a vacuum to the top section of the vacuum chamber through a duct a 253 that is connected to an orifice 260 in the wall of the chamber. Preferably the same vacuum source is used to draw a vacuum on the lower section of the vacuum chamber through a second duct 257 that is connected to a second orifice 255 in the wall of the vacuum chamber 263.

Again referring to FIG. 3, the apparatus is preferably integrated with an optical device 203, such as a spectrophotometer for measuring reflectance and transmitance. The spectrophotometer 203 is connected to a micro-processor 421 that is capable of computing disk layer thicknesses and disk layer compositions from reflectance and transmitance measurements. The micro-processor 421 is further connected to a stepper motor 208 to register the position of the sample and further provide information about the consistency of disk layers within a disk sample. The stepper motor 208 and the vacuum sources vacuum sources 207 and 205 are preferably controlled by a micro-processor that coordinates the operation of the raising, rotating and lowering of the sample.

In the most preferred embodiment, an apparatus rotationally re-positions a disk sample by raising, rotating and lowering the disk by the inner diameter region of the disk. The stationary stage has at least one side that does not protrude significantly past the inner diameter region of the disk in a direction parallel to the flat surface of the disk. Thus, a spectrophotometer can measure almost the entire surface of the disk side that is in contact with the stationary stage while the disk is being supported on the stage.

It will be clear to one skilled in the art that the above embodiments may be altered in many ways without departing from the scope of the invention. The sample contacting surfaces, the piston and platform or stage can be altered to suit various samples. The flat surface of the stationary stage is preferably metal but can be any material that can be machined to have a flat surface such as Teflon® or plastic. Stationary stage means rotationally stationary. The stage can be attached to second stage that is capable of translating the device in any direction relative to the device performing an operation or measurement. Accordingly, the scope of the invention should be determined by the following claims and their legal equivalents.

What is claimed is:

1. An apparatus for rotating and positioning a sample with a planar surface comprising;

a) a stationary stage with a flat surface for supporting said sample during an operation and a substantially central cylindrical bore with its length perpendicular to said flat surface;

b) a means for securing said sample to said flat surface;

c) a lifting aperture capable of moving upward, rotating and moving downward within said cylindrical bore;

d) a shaft connected to said lifting aperture, said shaft being capable of raising, rotating and lowering said lifting aperture;

e) a means for securing said sample to said lifting aperture during raising, rotating and lowering of said lifting aperture;

f) a means for rotating said shaft;

g) a means for raising said shaft; and h) a device for performing an operation;

whereby, said apparatus rotates and positions said planar sample on said flat surface of said stationary stage for said device to perform said operation on said plurality of positions of said planar surface of said sample at a repeatable distance and angle from said stationary device.

2. The apparatus of claim 1 wherein said lifting aperture is a cylindrical piston with a flat top portion.

3. The apparatus of claim 2 wherein said cylindrical piston is a metal piston.

4. The apparatus of claim 3 wherein said means for securing said sample to said flat top portion of said piston comprises a vacuum source that is draws a vacuum through an orifice in said flat top portion of said piston.

5. The apparatus of claim 1 wherein said stationary stage is a metal stage with a smooth machined flat surface.

6. The apparatus of claim 5 wherein said means for securing said planar sample to said smooth machined flat surface comprises a vacuum source that draws a vacuum through an orifice in said smooth machined flat surface.

7. The apparatus of claim 2 wherein said a means for securing said planar sample to said flat surface of said stage and said means for securing said sample to said flat top portion of said piston during raising, rotating and lowering of said sample is vacuum source that is drawn through an orifice in said flat top portion of said piston, whereby said piston is capable of recessing below said flat surface of said stationary stage.

8. The apparatus of claim 1 wherein said means for rotating said shaft comprises a first gear attached to said shaft and a second gear attached to a stationary motor, whereby said first gear and second gear engage when said shaft is in a raised position and said motor is capable of turning said shaft.

9. The apparatus of claim 8 wherein said motor is a stepper motor that registers a rotational position of said piston.

10. The apparatus of claim 2 wherein said means for lowering and raising said piston is selected from the group consisting of a spring, a pneumatic device and a solenoid.

11. The apparatus of claim 1 wherein stationary device for performing an operation comprises a spectrophotometer for measuring reflectance and transmitance.

12. The apparatus of claim 11 further comprising a computing micro-processor capable of analyzing the composition of said sample from reflectance and transmitance spectra.

13. An apparatus for rotating and positioning a disk;

a) a stationary stage with a flat surface for supporting said disk during an operation and a substantially central cylindrical bore with its length being perpendicular to said flat surface;

b) a cylindrical piston with a flat top portion, said piston being positioned within said bore and forming an essentially air tight seal between said piston and said bore;

c) a shaft connected to said piston, said shaft being capable of raising, rotating and lowering said piston;

d) a vacuum source that draws a vacuum through an orifice in said flat top potion of said piston and secures the disk during raising, rotating and lowering of said disk and further secures said disk to said flat surface of said stationary stage by receding below said flat surface of said stationary stage;

e) a means for raising said shaft;

f) a means for rotating said shaft;

g) a means for lowering said shaft; and h) a stationary device for performing an operation on said disk;

whereby, said apparatus rotates and positions said disk on said flat surface of said stationary stage for said device to perform said operation on a plurality of positions of disk at a repeatable distance and angle from said device.

14. The apparatus of claim 13 wherein said stationary stage is a metal stage with a smooth machined flat surface.

15. The apparatus of claim 13 wherein said cylindrical piston is a metal piston that capable of moving upward, rotating and moving downward within said cylindrical bore.

16. The apparatus of claim 13 wherein said a means for raising said piston is a spring that exerts a continuous upward forces on said shaft, whereby said piston is in a raised position in the absence of a greater downward force exerted on said shaft to overcome said continuous upward force of said spring.

17. The apparatus of claim 16 wherein said means for rotating said piston comprises a first gear attached to said shaft and a second gear attached to a stationary motor, whereby said first gear and second gear engage when said shaft is in said raised position and said motor is capable of turning said shaft.

18. The apparatus of claim 17 wherein said motor is a stepper motor that registers a rotational position of said piston.

19. The apparatus of claim 16 wherein said means for lowering said piston is a vacuum chamber comprising;

a) a section of said cylindrical bore that below said piston;

b) a means for drawing a vacuum in said section of said cylindrical bore, whereby said vacuum will cause said piston to lower; and c) a means for controlling the depth that said piston is lowered.

20. The apparatus of claim 19 wherein said means for drawing a vacuum in said section of said bore comprises a) a orifice in said bore;

b) a duct connected to said orifice; and c) a vacuum pump connected to said duct for drawing a vacuum through said duct and said section of said bore.

21. The apparatus of claim 19 wherein said means for controlling the depth that said piston is lowered is a piston stopper protruding from inside said bore such that said piston is prevented from lowering farther than the position that said piston contacts said piston stopper.

22. The apparatus of claim 13 wherein stationary device for performing an operation comprises a spectrophotometer for measuring reflectance and transmitance.

23. The apparatus of claim 13 further comprising a computing micro-processor capable of analyzing the composition of said sample from reflectance and transmitance spectra.

24. An apparatus for rotating and positioning a disk;

a) a stationary stage with a flat surface for supporting said disk during an operation and a substantially central cylindrical recession well with its length being perpendicular to said flat surface;

b) a circular disk platform with substantially the same diameter as said recession well and capable of moving upward and downward in said recession well, said disk platform connected to a shaft capable of raising said disk platform above said flat surface, rotating said disk platform and lowering said disk platform;

c) a vacuum source that draws a vacuum through said shaft to an orifice in said flat top potion of said circular disk platform and secures the disk during raising, rotating and lowering of said disk and further secures said disk to said flat surface of said stationary stage by receding below said flat surface of said stationary stage;

d) a means for raising said circular disk platform;

e) a means for rotating said circular disk platform; and f) a means for lowering said circular disk platform;

g) a device for performing an operation on said planar disk;

whereby, said apparatus rotates and positions said planar disk on said flat surface of said stationary stage for said device to perform said operation on a plurality of positions of said disk at a repeatable distance and angle from said device.

25. The apparatus of claim 24 wherein said stationary stage is a metal stage with a smooth machined flat surface.

26. The apparatus of claim 24 wherein said a means for raising said piston is a spring that exerts a continuous upward force on said shaft, whereby said shaft is in a raised position in the absence of a greater downward force exerted on said shaft to overcome said continuous upward force of said spring.

27. The apparatus of claim 26 wherein said means for rotating said piston is a gear assembly comprising a first gear attached to said shaft and a second gear attached to a stationary motor, whereby said first gear and second gear engage when said shaft is in said raised position and said motor is capable of turning said shaft.

28. The apparatus of claim 27 wherein said motor is a stepper motor that registers a rotational position of said disk platform.

29. The apparatus of claim 26 wherein said means for lowering said circular disk platform comprises:

a) a cylindrical vacuum chamber positioned between said recession well and said gear assembly, said cylindrical vacuum chamber having a predetermined diameter and length whereby said length of said vacuum chamber is parallel to said shaft and said shaft passes through the center of said chamber;

b) a piston housed within said chamber and attached to said shaft;

b) a means for drawing a vacuum on a bottom portion of said piston and vacuum chamber, whereby said vacuum will cause said piston said shaft and said disk platform to move downward; and c) a means for controlling the depth that said piston is lowered.

30. The apparatus of claim 29 wherein a means for drawing a vacuum in said chamber comprises a) a orifice in said chamber and below said bottom of said piston;

b) a duct connected to said orifice; and c) a vacuum pump connected to said duct for drawing a vacuum through said duct and camber bore below said piston.

31. The apparatus of claim 29 wherein said means for controlling the depth that said disk platform is lowered is the physical contact between said recession well and said disk platform.

32. The apparatus of claim 24 wherein said stationary device for performing an operation comprises a spectrophotometer for measuring reflectance and transmitance.

33. The apparatus of claim 32 wherein said spectrophotometer for measuring reflectance and transmitance measures reflectance and transmitance from a side of a disk sample that is in contact with said stationary stage.

34. The apparatus of claim 32 further comprising a computing micro-processor capable of analyzing the composition of said sample from reflectance and transmitance spectra.

35. The apparatus of claim 24 wherein said disk platform further comprises a raised circular portion positioned centrally on said disk platform whereby a disk with a central circular cut out will be held centrally on said disk platform.

36. The apparatus of claim 35 wherein said means for lowering said circular disk platform comprises:

a) a cylindrical chamber positioned between said recession well and said gear assembly, said chamber having a predetermined diameter and length whereby said length of said chamber is parallel to said shaft and said shaft passes through the center of said chamber;

b) a first cylindrical piston with a diameter substantially equal to said predetermined diameter of said a cylindrical chamber with said first piston being capable of sliding upward and downward on said shaft that passes though the center of said first piston;

c) a stop ring attached to said shaft below said first piston whereby said stop ring prevents said first piston from sliding downward on said shaft past a point on said shaft that said stop ring is attached;

d) a first piston stop positioned in said chamber at a predetermined depth below said first piston in said chamber to prevent said first piston from moving downward in said chamber past said predetermined depth;

e) a second piston stop positioned in said chamber at a predetermined depth below said first piston stop in said chamber;

f) a second cylindrical piston positioned below said second piston stop with a diameter substantially equal to said predetermined diameter of said a cylindrical chamber, said second piston being capable of sliding up and down said shaft that passes though the center of said second piston, whereby said second piston in prevented from moving upward past said second piston stop;

g) a means to draw a vacuum on said chamber between said first piston and said second piston;

h) a second stop ring attached to said shaft to whereby said stop ring prevents said second piston from sliding upward on shaft past a point on said shaft that said stop ring is attached; and i) a means to draw a vacuum on said chamber below said second piston;

whereby, drawing a vacuum on said chamber between said first piston and said second piston lowers said disk platform to a first level and drawing a vacuum on said chamber below said second piston further lowers said disk platform to a second level.

37. The apparatus of claim 36 wherein a means for drawing said vacuum on said chamber between said first piston and said second piston comprises:

a) an orifice on the a wall of said cylindrical chamber positioned between first piston stop and said second piston stop said first piston;

b) a duct connected to said orifice; and c) a vacuum pump connected to said duct for drawing a vacuum through said duct and portion of said bore below said piston.

38. The apparatus of claim 35 wherein a means for drawing said vacuum on said chamber below said second piston comprises:
  a) an orifice on the a wall of said cylindrical chamber positioned between said bottom portion of said second piston and said bottom of said cylindrical chamber;
  b) a duct connected to said orifice; and
  c) a vacuum pump connected to said duct for drawing a vacuum through said duct and portion of said bore below said piston.

39. The apparatus of claim 24 further comprising a second stage mounted to said stationary stage to reposition said stationary stage and said sample relative said device for performing an operation.

40. The apparatus of claim 24 wherein said disk platform further comprises a raised circular portion positioned centrally on said disk platform whereby a disk with a central circular cut out will be held centrally on said disk platform.

* * * * *

UNITED STATES PATENT AND TRADEMARK OFFICE
CERTIFICATE OF CORRECTION

PATENT NO. : 6,084,666
DATED : July 4, 2000
INVENTOR(S) : Alexander P. Kindwall

It is certified that error appears in the above-identified patent and that said Letters Patent is hereby corrected as shown below:

On the title page:

Section [73] Change "N+K Technology, Inc." to --n&k Technology, Inc.--

Signed and Sealed this

Twenty-fourth Day of April, 2001

Attest:

NICHOLAS P. GODICI

Attesting Officer        Acting Director of the United States Patent and Trademark Office